United States Patent [19]

Renfroe

[11] 4,436,746

[45] Mar. 13, 1984

[54] THROMBOXANE SYNTHETASE INHIBITORY N-SUBSTITUTED-2-(1-IMIDAZOLYL)INDOLES

[75] Inventor: Harris B. Renfroe, West Nyack, N.Y.

[73] Assignee: Ciba-Geigy Corporation, Ardsley, N.Y.

[21] Appl. No.: 430,644

[22] Filed: Sep. 30, 1982

[51] Int. Cl.³ .................. A61K 31/415; C07D 403/04
[52] U.S. Cl. ................................. 424/273 R; 548/336
[58] Field of Search .................... 548/336; 424/273 R

[56] References Cited

U.S. PATENT DOCUMENTS

| | | | |
|---|---|---|---|
| 3,454,586 | 7/1969 | Suh | 548/336 X |
| 4,059,583 | 11/1977 | McComsey et al. | 548/336 X |
| 4,140,858 | 2/1979 | Zinnes et al. | 548/336 |
| 4,217,357 | 8/1980 | Cross et al. | 424/273 R |
| 4,273,782 | 6/1981 | Cross et al. | 424/273 R |

OTHER PUBLICATIONS

Abstracts, North American Medicinal Chemistry Symposium (1980), p. 68.

*Primary Examiner*—Richard A. Schwartz
*Attorney, Agent, or Firm*—Norbert Gruenfeld

[57] ABSTRACT

Various 1-carboxylic acid substituted-2-(1-imidazolyl)indoles and functional derivatives thereof are highly specific thromboxane synthetase inhibitors. Synthesis of, pharmaceutical compositions thereof, and methods of treatment utilizing such compounds are included.

9 Claims, No Drawings

THROMBOXANE SYNTHETASE INHIBITORY N-SUBSTITUTED-2-(1-IMIDAZOLYL)INDOLES

SUMMARY OF THE INVENTION

The present invention is concerned with N-(or 1)-substituted-2-(1-imidazolyl)indoles of formula I representing a novel class of pharmaceuticals. For example, the compounds of formula I are surprisingly potent and highly specific thromboxane synthetase inhibitors.

The foregoing attributes render the N-substituted-2-(1-imidazolyl)indoles of this invention particularly useful when administered, alone or in combination, to mammals, e.g. for the treatment or prevention of diseases responsive to the inhibition of thromboxane synthetase, comprising cardiovascular disorders such as thrombosis, atherosclerosis, coronary spasm, cerebral ischaemic attacks, migraine and other vascular headaches, myocardial infarction, angina pectoris, hypertension; respiratory disorders, such as asthma; and inflammatory disorders. Inhibition of thromboxane synthetase also has been noted to decrease metastasis in certain classes of tumors, and the compounds of this invention may thus be useful for the treatment of certain carcinomas.

This invention relates to N(or 1)-substituted-2-(1-imidazolyl)-indoles of formula I which are useful as selective thromboxane synthetase inhibitors, processes for preparing same, pharmaceutical compositions comprising said compounds, and methods of treating syndromes, conditions and diseases in mammals responsive to the inhibition of thromboxane synthetase by administration of said compounds and compositions.

Particularly the invention relates to the 1-substituted 2-(1-imidazolyl)-indoles of formula I

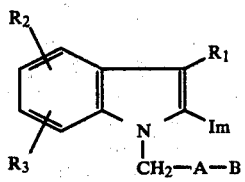

wherein $R_1$ represents hydrogen or lower alkyl;

Im represents 1-imidazolyl unsubstituted or substituted by lower alkyl, carboxy, lower alkoxycarbonyl or carbamoyl;

$R_2$ and $R_3$ independently represent hydrogen, lower alkyl, halogen, trifluoromethyl, hydroxy, lower alkoxy, lower alkyl-(thio, sulfinyl or sulfonyl); or $R_2$ and $R_3$ together when attached to adjacent carbons represent lower alkylenedioxy;

A represents straight chain or branched alkylene of 1 to 12 carbon atoms, alkenylene of 2 to 12 carbon atoms, alkynylene of 2 to 12 carbon atoms, lower alkylenephenylene lower alkylene, lower alkylenephenylene, phenylene lower alkylene, phenylene, a direct bond, lower alkylene-(thio or oxy)-lower alkylene, lower alkylene-(thio or oxy)-phenylene;

B represents carboxy, lower alkoxycarbonyl, carbamoyl, mono- or di-lower alkylcarbamoyl, cyano or hydroxymethyl; the N-oxides thereof; and pharmaceutically acceptable salts thereof.

DETAILED DESCRIPTION OF THE INVENTION

Preferred embodiments of this invention relate to compounds of formula I wherein $R_1$ represents hydrogen or lower alkyl;

Im represents 1-imidazolyl unsubstituted or substituted by lower alkyl;

$R_2$ is hydrogen, lower alkyl, halogen, trifluoromethyl, hydroxy, lower alkoxy;

$R_3$ is hydrogen;

A represents straight chain or branched alkylene of 1 to 12 carbon atoms, phenylene, lower alkylenephenylene or lower alkylene-(thio or oxy)-phenylene of 7 to 10 carbon atoms each, or a direct bond;

B represents carboxy, lower alkoxycarbonyl, carbamoyl, cyano or hydroxymethyl; the N-oxides thereof; and pharmaceutically acceptable salts thereof.

Further preferred are said compounds wherein $R_2$ is attached at the 5-position of the indole nucleus.

Very useful as thromboxane synthetase inhibitors are compounds of formula I wherein A represents straight chain or branched alkylene of 1 to 12 carbon atoms.

Particularly useful are compounds of formula II

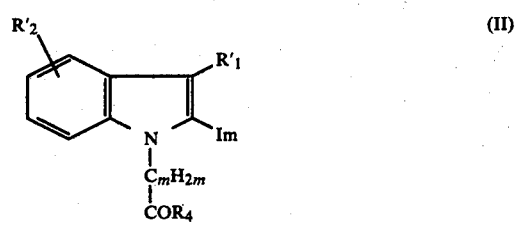

wherein $R_1'$ represents hydrogen or lower alkyl;

$R_2'$ represents hydrogen, lower alkyl, halogen, trifluoromethyl, hydroxy or lower alkoxy;

Im represents 1-imidazolyl;

m represents an integer from 1 to 13;

$R_4$ represents hydroxy, lower alkoxy or amino; and pharmaceutically acceptable salts thereof.

Especially valuable are compounds of formula II wherein $R_1'$ represents methyl, ethyl, propyl;

$R_2'$ represents hydrogen, methyl, chloro, fluoro, trifluoromethyl, hydroxy or methoxy;

m represents an integer from 3 to 10;

$R_4$ represents hydroxy, ethoxy, methoxy or amino;

Im represents 1-imidazolyl; and pharmaceutically acceptable salts thereof.

Most preferred are the compounds of formula II wherein $R_1'$ represents methyl, $R_2'$ represents hydrogen, m is 4 to 8, Im represents 1-imidazolyl, and $R_4$ represents hydroxy, ethoxy, methoxy or amino.

Also valuable are compounds of formula III

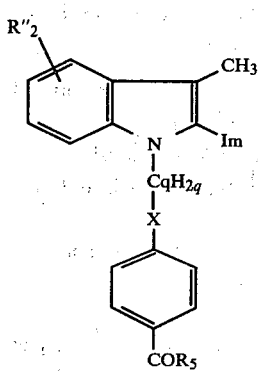

(III)

wherein :
R₂″ represents hydrogen, methyl, chloro, fluoro, trifluoromethyl, hydroxy or methoxy;
q represents an integer from 1 to 4;
X=oxygen, sulfur or a direct bond;
R₅ represents hydroxy or lower alkoxy;
Im represents 1-imidazolyl; and pharmaceutically acceptable salts thereof.

Preferred are compounds of formula III wherein q=1; Im=1-imidazolyl; R₅=hydroxy; and X=a direct bond. Also preferred are compounds of formula III wherein q=2; R₅=OH; and X=O or S.

The general definitions used herein have the following meanings within the scope of the present invention.

A straight chain or branched alkylene represents C₁₋₁₂ alkylene preferably propylene, butylene, pentylene, hexylene, or heptylene, said radicals being unsubstituted or substituted by one or more lower alkyl groups with the proviso that the total number of carbon atoms equals no more than 12.

The term "straight chain or branched alkenylene" represents C₂₋₁₂ alkenylene groups preferably propenylene, 1- or 2-butenylene 1- or 2-pentenylene, 1-, 2- or 3-hexenylene, 1-, 2-, 3 or 4-heptenylene, said groups being unsubstituted or substituted by one or more lower alkyl groups with the proviso that the total number of carbon atoms equals no more than 12.

The term "straight chain or branched alkynylene" represents C₂-C₁₂ alkynylene preferably propynylene, 1- or 2-butynylene, 1- or 2-pentynylene, 1-, 2- or 3-hexynylene, 1-, 2-, 3- or 4-heptynylene, said radicals being unsubstituted or substituted by one or more lower alkyl groups with the proviso that the total number of carbon atoms equals no more than 12. The term phenylene represents 1,2-, 1,3- and preferably 1,4-phenylene.

The term "lower" when referred to above and hereinafter in connection with organic groups, radicals or compounds respectively defines such with up to and including 7, preferably up to and including 4 and advantageously one, two or three carbon atoms.

A lower alkylenephenylene group, a phenylene lower alkylene group or a lower alkylenephenylene lower alkylene group preferably contains 1 to 4 carbon atoms and advantageously one or two carbon atoms in each alkylene portion.

A lower alkyl group preferably contains 1-4 carbon atoms and represents for example ethyl, propyl, butyl or advantageously methyl.

A lower alkylenedioxy group represents preferably ethylenedioxy and methylenedioxy.

A lower alkoxy group preferably contains 1-4 carbon atoms and represents for example, ethoxy, propoxy or advantageously methoxy. A lower alkyl-(thio, sulfinyl or sulfonyl) group represents advantageously methylthio, methylsulfinyl or methylsulfonyl respectively.

A lower alkoxycarbonyl group preferably contains 1-4 carbon atoms in the alkoxy portion and represents for example: methoxycarbonyl, propoxycarbonyl, isopropoxycarbonyl or advantageously ethoxycarbonyl. A mono(lower alkyl) carbamoyl group preferably contains 1-4 carbon atoms in the alkyl portion and is for example N-methylcarbamoyl, N-propylcarbamoyl, or advantageously N-ethylcarbamoyl. A di(lower alkyl) carbamoyl group preferably contains 1-4 carbon atoms in each lower alkyl portion and represents for example N,N-dimethylcarbamoyl, N-methyl-N-ethylcarbamoyl and advantageously N-N-diethylcarbamoyl.

Halogen is preferably fluorine and chlorine, but may also represent bromine or iodine.

Pharmaceutically acceptable salts are preferably metal or ammonium salts or said compounds of formula I having a free carboxy group, more particularly alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amines, lower alkylenediamines or lower (hydroxyalkyl or aralkyl)-alkylammonium hydroxides, e.g., methylamine, diethylamine, triethylamine, dicyclohexylamine, triethanolamine, ethylenediamine, tris(hydroxymethyl)aminomethane or benzyltrimethylammonium hydroxide. Said compounds of Formula I form acid addition salts of preferably the pharmaceutically acceptable inorganic or organic acids, such as of strong mineral acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycolic, lactic, malic, tartaric, gluconic, citric, ascorbic, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic or cyclohexylsulfamic acid.

The compounds of this invention exhibit valuable pharmacological properties, e.g. cardiovascular effects, by selectively decreasing thromboxane levels through selective inhibition of thromboxane synthetase in mammals. The compounds are thus useful for treating diseases responsive to thromboxane synthetase inhibition in mammals, primarily cardiovascular disorders such as thrombosis, atherosclerosis, coronary spasm, cerebral ischaemic attacks, migraine and other vascular headaches, myocardial infarction, angina pectoris, and hypertension.

These effects are demonstrable in in vitro tests or in vivo animal tests using advantageously mammals, e.g. guinea pigs, mice, rats, cats, dogs, or monkeys. Said compounds can be administered to them enterally or parenterally, advantageously orally, or subcutaneously, intravenously or intraperitoneally, for example, within gelatin capsules, or in the form of starchy suspensions or aqueous solutions respectively. The applied dosage may range between about 0.01 to 100 mg/kg/day, preferably between about 0.05 and 50 mg/kg/day, advantageously between about 0.1 and 25 mg/kg/day.

The in vitro inhibition of the thromboxane synthetase enzyme can be demonstrated, analogous to the method of Sun, Biochem. Biophys. Res. Comm. 74, 1432 (1977); the testing procedure is as follows:

$^{14}$C-Arachidonic acid is incubated with an enzyme consisting of solubilized and partially purified prostaglandin cyclo-oxygenase from sheep seminal vesicles and a crude microsomal preparation of thromboxane synthetase from lysed human platelets. The test compound (dissolved in buffer, or if necessary, in a small amount of ethanol) is added to the incubation medium. At the end of the incubation period (30 minutes), Prostaglandin E2 (PGE$_2$) is reduced to a mixture of Prostaglandin F$_2\alpha$ and F$_2\beta$ (PGF$_2\alpha+\beta$) by addition of sodium borohydride. The radioactive products and excess substrate are extracted into ethyl acetate; the extract is evaporated to dryness; the residue is dissolved in acetone, spotted on thin-layer plates and chromatographed in the solvent system toluene:acetone:glacial acetic acid (100 volumes:100 volumes:3 volumes). The radioactive zones are located; those corresponding to Thromboxane B$_2$ (TxB$_2$) and PGF$_2\alpha+\beta$ are transferred to liquid scintillation vials and counted. The ratio of counts for TxB$_2$/PGF$_2\alpha+\beta$ is calculated for each concentration of test compound and IC$_{50}$ values are determined graphically as the concentration of test compound at which the ratio of TxB$_2$PGF$_2\alpha+\beta$ is reduced to 50% of the control value.

The in-vitro effect on prostaglandin cyclooxygenase is measured by a modification of the method of Takeguchi et al. described in Biochemistry 10, 2372 (1971); the testing procedure is as followes:

Lyophilized sheep seminal vesicle microsomes are utilized as the prostaglandin-synthesizing enzyme preparation. The conversion of $^{14}$C-arachidonic acid to PGE$_2$ is measured. Test compounds (dissolved in buffer, or if necessary, in small amount of ethanol) are added to the incubation mixture. The prostaglandins are extracted and separated by thin-layer chromatography; the plates are scanned, the radioactive zones corresponding to PGE$_2$ are transferred to liquid scintillation vials and counted for radioactivity. IC$_{50}$ values for inhibition are determined graphically as the concentration of test compound causing a 50% reduction in the amount of PGE$_2$ synthesized.

The in-vitro effect on prostacyclin (PGI$_2$) synthetase is measured analogous to the method of Sun et al., Prostaglandins 14, 1055 (1977);

The testing procedure is as follows:

$^{14}$C-Arachidonic acid is incubated with an enzyme mixture consisting of solubilized and partially purified prostaglandin cyclo-oxygenase from sheep seminal vesicles and crude PGI$_2$ synthetase in the form of a microsomal fraction of bovine aorta.

Test compound (dissolved in buffer, or if necessary, in a small amount of ethanol) is placed in the incubation medium. The reaction mixture is incubated in 100 mM Tris HCl (pH 7.5) for 30 minutes at 37° C., acidified to pH 3 and extracted into ethyl acetate. The extract is evaporated to dryness; the residue is dissolved in acetone, spotted on thin-layer plates and chromatographed in a solvent system described by Sun et al. The radioactive zones are located with a scanner; those corresponding to 6-keto-PGF$_1\alpha$ (a stable end product of prostacyclin biotransformation) and PGE$_2$ are transferred to liquid scintillation vials and counted. The ratio of counts for 6-keto-PGF$_1\alpha$/PGE$_2$ is calculated for each concentration of test compound used. IC$_{50}$ values for inhibition are determined graphically as the concentration of test compound at which the ratio of 6-keto-PGF$_1\alpha$/PGE$_2$ is reduced to 50% of the control value.

The inhibition of the synthesis and the reduction of plasma levels of thromboxane is determined in vivo on administration to rats in the following manner (as adapted from the procedures described by Tai et al. in Anal. Biochem. 87: 343, 1978 and by Salmon in Prostaglandins 15: 383, 1978):

Rats are dosed with vehicle or test drug and injected intravenously with ionophore A23187 (0.5 mg/kg) two hours later. Blood is collected for analysis 2 minutes after the ionophore injection. A single aliquot of each plasma sample is assayed for thromboxane B$_2$ and another aliquot for 6-keto-PGF$_1\alpha$, the stable metabolites of thromboxane A$_2$ and prostacyclin (PGI$_2$) respectively, by radioimmunoassay.

Compounds of the formula I are very potent and selective thromboxane synthetase inhibitors. At and above the effective dose levels for thromboxane synthetase inhibition neither the beneficial prostacyclin synthetase enzyme system nor the prostaglandin cyclooxygenase enzyme system is significantly inhibited.

Illustrative of the invention, the IC$_{50}$ for 1-(5-carboxypentyl)-3-methyl-2-(1-imidazolyl)indole hydrochloride is $2.3\times10^{-9}$ M for thromboxane synthetase inhibition.

Further illustrative of the invention, 1-(5-carboxypentyl-3-methyl-2-(1-imidazolyl)-indole hydrochloride decreases the plasma concentration of thromboxane B$_2$ by over 50% in the rat at an oral dose as low as 0.20 mg/kg; an increase in the plasma level of prostacyclin occurs at this or a higher dose thereof.

The aforementioned advantageous properties render the compounds of this invention of great value as specific therapeutic agents for the treatment of diseases responsive to the inhibition of thromboxane synthetase in mammals including man, e.g. for the treatment of cardiovascular diseases such as thromboembolism.

In addition to the pharmaceutically acceptable salts cited above, any prodrug derivatives thereof, e.g., pharmaceutically acceptable esters and amides of the carboxylic acids of this invention that may be convertible by solvolysis or under physiological conditions to the said carboxylic acids, represent a further object of this invention.

Said esters are preferably e.g., the straight chain or branched lower alkyl esters unsubstituted or suitably substituted such as the pivaloyloxymethyl, 2-diethylaminoethyl, α-carboxyethyl or suitably esterified α-carboxyethyl esters and the like which are prepared by methods well known to the art.

Said amides are preferably e.g. simple primary and secondary amides and amides derived from the amino acids or derivatives thereof, such as the amides derived from alanine, phehylalanine and the like.

The compounds of formula I are advantageously prepared according to the following process:

(1) condensing a compound of the formula IV

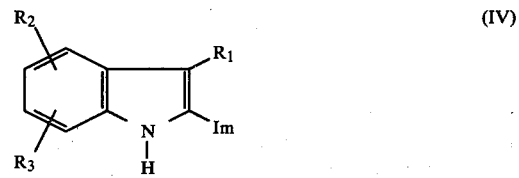

(IV)

wherein $R_1$, $R_2$, $R_3$ and Im have meaning as previously defined;

with a reactive functional derivative of a compound of the forlula V

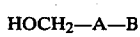

HOCH$_2$—A—B    (V)

wherein A and B have meaning as previously defined, with optional temporary protection of interfering reactive groups; and optionally (b) converting any resulting compound into another compound of formula I.

The compounds of the invention may also be prepared by (2) converting into a compound of formula I a compound of formula Ia

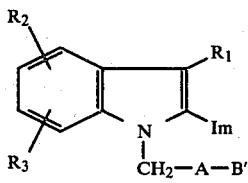

(Ia)

wherein A, Im, $R_1$, $R_2$ and $R_3$ have meaning as previously defined and B' represents a group convertible into B with optional extension of the chain A within definition, e.g. trialkoxymethyl, etherified and esterified hydroxymethyl or halomethyl;

The synthesis of compounds of formula Ia is carried out by reacting an indole of formula IV with a reactive functional derivative of a compound of the formula VI

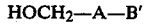

HOCH$_2$—A—B'    (VI)

wherein A and B' are as defined above.

Indoles of formula IV are converted preferably in situ, to reactive intermediates with preferably about one molar equivalent of e.g. a strong base, preferably of an alkali metal such as lithium diisopropylamide, sodium hydride, potassium t-butoxide, or tetrabutylammonium hydroxide in an inert solvent such as dimethylformamide, acetonitrile or tetrahydrofuran at a temperature range between −50° to +75° preferably between −25° and +50°. Condensation of the resulting reactive intermediate with a reactive functional derivative of a compound of formula V or VI proceeds at a temperature range from about −25° to +50° preferably at a temperature range of 0° to 30°. In the case where B represents carboxy, carbamoyl, mono lower alkylcarbamoyl, additional, e.g. one molecular equivalent, of base is required.

The novel intermediates of formula IV are advantageously prepared by condensation of the corresponding 2-unsubstituted indole of formula VII

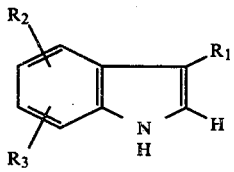

(VII)

wherein $R_1$, $R_2$ and $R_3$ have meaning as previously described, with a compound of the formula ImH, wherein Im has meaning as previously described, in the presence of a halogen, preferably bromine in an inert solvent, such as dioxane, at a temperature range of 0° to 100°, advantageously at room temperature.

The starting materials of formula V and VI are known or if new, are prepared according to conventional methods, e.g. the methods illustrated in U.S. Pat. No. 4,256,757, British patent application No. 2,016,452A or as described in the examples herein.

The indoles of formula VII are known or if new are prepared by conventional methods well known in the art.

Certain terms used in the foregoing processes have the meanings as defined below.

Reactive functional derivatives of alcohols of formula V and VI are e.g. such esterified by a strong inorganic or organic acid above all a hydrohalic acid, e.g. hydrochloric, hydrobromic or hydriodic acid, an aliphatic or aromatic sulfonic acid, e.g. methanesulfonic acid, p-toluenesulfonic acid, and are prepared by methods known in the art.

Trialkoxymethyl represents preferably tri(lower alkoxy)-methyl, particularly triethoxy- or trimethoxymethyl.

Etherified hydroxymethyl represents preferably tertiary lower alkyloxymethyl, lower alkoxyalkoxymethyl such as methoxymethyloxymethyl, 2-oxa- or 2-thiacycloalkoxymethyl particularly 2-tetrahydropyranyloxymethyl.

Esterified hydroxymethyl represents preferably lower alkanoyloxymethyl, e.g. acetyloxymethyl.

Halomethyl represents especially chloromethyl but may also br bromomethyl or iodomethyl.

An alkali metal represents preferably lithium but may also be potassium or sodium.

The conversion of a compound of formula Ia into a compound of formula I, e.g. by hydrolyzing or derivatizing a product Ia of the aforesaid process, and the conversion of a product of formula I into another compound of this invention are performed by chemical methodology known to the art.

Hydrolysis of intermediates of formula Ia wherein B' represents trialkoxymethyl to compounds of formula I wherein B is carboxy is advantageously carried out with inorganic acids such as hydrohalic or sulfuric acid. Hydrolysis of intermediates wherein B' represents etherified hydroxymethyl to compounds of formula I wherein B represents hydroxymethyl is preferably carried out with solutions of inorganic acids such as a hydrohalic acid.

The compounds of formula Ia wherein B' is halomethyl are converted to compounds of formula I, wherein B is carboxy and the chain length is extended by two carbons, by first treating with e.g. a di(lower)alkylmalonate followed by hydrolysis and decarboxylation under standard conditions.

Intermediates of formula Ia wherein B' is halomethyl may be reacted preferably with a alkali metal cyanide such as potassium cyanide in a conventional manner to yield the compounds of formula I wherein the chain is extended by 1 carbon atom and B is cyano. These in turn are converted to compounds of formula I wherein B is carboxy, alkoxycarbonyl or carbamoyl using methods known to the art.

Compounds of formula I wherein A represents lower alkylene or a direct bond and B represents hydroxymethyl, as reactive functional derivatives thereof, may be condensed with a lower alkanol (or thiol) or a phenol (or thiophenol) appropriately substituted by B, preferably in the presence of a strong base, to give compounds of formula I wherein A represents lower alkylene-(thio or oxy)-phenylene, phenylene-(thio or oxy)-lower alkylene or lower alkylene-(thio or oxy)-lower alkylene.

Compounds of formula I wherein B is lower alkoxycarbonyl may be amidized with ammonia, mono- or di-(lower) alkylamines to yield compounds of formula I wherein B represents unsubstituted, mono- or di-(lower) alkylcarbamoyl.

The compounds of formula I wherein B represents unsubstituted carbamoyl may be dehydrated to the corresponding nitriles by methods known to the art. Conversion of compounds of formula I wherein B is lower alkoxycarbonyl; cyano; unsubstituted, mono- or di-(lower alkyl)carbamoyl to compounds of formula I wherein B represents carboxy is advantageously carried out by hydrolysis with inorganic acids such as hydrohalic or sulfuric acid or with aqueous alkalies preferably alkali metal hydroxides such as lithium or sodium hydroxide.

Compounds of formula I wherein B represents carboxy or lower alkoxycarbonyl may be reduced with simple or complex light metal hydrides such as lithium aluminum hydride, alane or diborane to compounds of formula I wherein B is hydroxymethyl. Said alcohols are also obtained by appropriate solvolysis of compounds of formula Ia wherein B' is halomethyl.

Said alcohols may in turn be transformed to the compounds of formula I wherein B is carboxy with conventional oxidizing agents.

Free carboxylic acids may be esterified with unsubstituted or substituted lower alkanols or diazo (lower) alkanes to give the corresponding esters, namely compounds of formula I wherein B is lower alkoxycarbonyl. Furthermore, the free carboxylic acids may be converted via reactive intermediates to compounds of formula I wherein B represents unsubstituted, mono or di-(lower)alkylcarbamoyl.

Compounds of formula I wherein B represents mono(lower) alkylcarbamoyl may be converted to compounds of formula I wherein B is di(lower)alkylcarbamoyl by treatment of the former with a strong base e.g. sodium hydride followed by an alkylating agent, e.g. a lower alkyl halide in an inert solvent, e.g. dimethylformamide.

Furthermore compounds of formula I wherein A represents a straight chain or branched alkynylene or alkenylene may be converted by catalytic hydrogenation e.g. under neutral conditions to compounds of formula I wherein A represents straight chain or branched alkylene.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably at the boiling point of the solvents used, and at atmospheric or superatmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially useful.

The invention also relates to novel starting materials and processes for their manufacture.

Depending on the choice of starting materials and methods, the new compounds may be in the form of one of the possible isomers or mixtures thereof, for example, depending on the presence of a double bond and the number of asymmetrical carbon atoms, as pure optical isomers, such as antipodes, or as mixtures of optical isomers such as racemates, mixtures of diastereoisomers, mixtures of racemates or mixtures of geometrical isomers. The aforesaid possible isomers or mixtures thereof are within the purview of this invention; certain particular isomers may be preferred.

Any resulting mixtures of diastereoisomers, mixtures of racemates and geometric isomers can be separated on the basis of the physicochemical differences of the constituents, in known manner, into the pure isomers, diastereoisomers, racemates, or geometric isomers, for example by chromatography and/or fractional crystallisation.

Any resulting racemates can be resolved into the optical antipodes by known methods, for example by e.g. reacting an acidic end product with an optically active base that forms salts with the racemic acid, and separating the salts obtained in this manner, for example by fractional crystallization, into the diastereoisomeric salts from which the optically active carboxylic acid antipodes can be liberated on acidification. The basic racemic products can likewise be resolved into the optical antipodes, e.g. by separation of the diastereoisomeric salts thereof with an optically active acid, and liberating the optically active basic compound by treatment with a standard base. Racemic products of the invention can thus be resolved into their optical antipodes, e.g., by the fractional crystallizatin of d- or l-(tartrates, mandelates, camphorsulfonates, or of d- or l-(α-methylbenzylammonium, cinchonidine, cinchonine, quinine, quinidine, ephedrine, dehydroabiethylamine, brucine or strychnine)salts. Advantageously, the more active of the two antipodes is isolated.

Finally, the compounds of the invention are either obtained in the free form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation. A compound of formula I wherein B represents carboxy can thus also be converted into the corresponding metal or ammonium salts. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solents used for their crystallization.

The pharmaceutical compositions according to the invention are those suitable for enteral, such as oral or rectal, and parenteral administration to mammals, including man, for the treatment or prevention of diseases responsive to inhibition of thromboxane synthetase, comprising an effective amount of a pharmacologically active compound of formula I, or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets aldo (c) binders, e.g. magnesium aluminum silicate, starch paste, gelatin, tragacanth, methylcellulose, sodium carboxymethylcellulose and/or polyvinylpyrrolidone; if desired (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solutions promotes, salts for regulating the osmotic pressure and/or buffers. In addition, they may also contan other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 kg may contain between about 10 to 100 mg of the active ingredient.

The following examples are intended to illustrate the invention and are not to be construed as being limitations thereon. Temperatures are given in degrees centigrade, and all parts wherever given are parts by weight. If not mentioned otherwise, all evaporations are performed under reduced pressure, preferably between about 15 and 100 mmHg.

EXAMPLE 1

To a suspension of 60% sodium hydride (0.34 g) in dimethylformamide (10 ml), while stirring under nitrogen at 0°–5°, is added dropwise a solution of 2-(1-imidazolyl)-3-methyl-indole (1.50 g) in dimethylformamide (15 ml). Upon complete addition the mixture is stirred at 0°–5° for 1 hr. To the nearly complete solution is added methyl 6-bromohexanoate (1.67 g) dropwise. The mixture is stirred at 0°–5° for 0.5 hr, then for two days at room temperature. The solution is poured into water (100 ml) and extracted with ethyl acetate (3×50 ml), dried (MgSO$_4$), filtered, and concentrated in vacuo to give an amber oil which is stirred with 100 ml of petroleum ether for 15 minutes. The mixture is placed in a separatory funnel and the insoluble amber oil separated and removed. The oil is dried in vacuo to give 1-(5-methoxycarbonylpentyl)-2-(1-imidazolyl)-3-methylindole as an oil; NMR (CDCl$_3$): δ3.60(3H), 3.90(2H).

The indole starting material is prepared as follows:

To a solution of 3-methylindole (7.87 g) and imidazole (20.42 g) in dioxane (350 ml) stirring at 10° is added a solution of bromine (3.1 ml) in dioxane (125 ml) dropwise over a period of 25 hrs. Upon complete addition, the cooling bath is removed and the resulting yellow suspension is allowed to warm to room temperature while stirring overnight. The solid which had formed is removed by vacuum filtration. The filtrate is concentrated in vacuo to give an amber oil. This oil is suspended in 2 N HCl (100 ml) and washed with ether (3×100 ml). The acidic layer is made basic to pH 10 with 3 N NaOH and extracted with ether (6×100 ml). The ether extract is dried (MgSO$_4$), filtered and concentrated in vacuo to give a partially crystalline residue. This residue is triturated with petroleum ether/ether and the solid which resulted is collected and recrystallized from acetonitrile (30 ml) to give 2-(1-imidazolyl)-3-methylindole, m.p. 156°–158°.

Methyl 6-bromohexanoate is prepared as follows:

A solution of 6-bromohexanoic acid (10 g) in 50 ml of methanol to which was added 1.0 ml of concentrated sulfuric acid is heated under reflux for 8 hours. The methanol is distilled off, the residue is dissolved in ether. The ether solution is washed free of acid with water, dried over sodium sulfate and evaporated to dryness. Distillation at 0.8 mm Hg gives methyl 6-bromohexanoate, b.p. 85°–90°/0.8 mm.

EXAMPLE 2

In a similar manner is prepared 1-(4-ethoxycarbonylbutyl)-2-(1-imidazolyl)-3-methylindole; NMR (CDCl$_3$): 1.20 (3H), 4.07 (2H), 3.90 (2H).

EXAMPLE 3

A mixture of 1-(5-methoxycarbonylpentyl)-2-(1-imidazolyl)-3-methylindole (1.80 g) and 30 ml of 3 N NaOH is stirred at room temperature for 1.3 hours. The resulting clear, yellow solution is neutralized to pH 6 with 2 N HCl. The resulting suspension is extracted with ethyl acetate (2×50 ml). The organic extract is washed with a saturated NaCl solution (1×25 ml), dried (MgSO$_4$), filtered, and concentrated in vacuo to give a cream-colored solid. The solid is dissolved in ethanol and the solution treated with 0.6 ml of 6.5 N HCl in ethanol. The solution is diluted with diethyl ether and after standing for several hours the precipitate whch forms is collected by filtration to give 1-(5-carboxypentyl)-2-(1-imidazolyl)-3-methylindole hydrochloride, m.p. 177.5°–180.5° dec.

EXAMPLE 4

In a similar manner is prepared 1-(4-carboxybutyl)-2-(1-imidazolyl)-3-methylindole hydrochloride, m.p. 204°–206°.

EXAMPLE 5

Compounds of formula II in which Im represents 1-imidazolyl which are prepared by the methods described herein.

| Compound | R'$_1$ | R'$_2$ | C$_m$H$_{2m}$ | R$_4$ |
|---|---|---|---|---|
| 5/1 | CH$_3$ | 5-Cl | (CH$_2$)$_5$ | OH |
| 5/2 | CH$_3$ | 5-OCH$_3$ | (CH$_2$)$_5$ | OH |
| 5/3 | CH$_3$ | 5-CH$_3$ | (CH$_2$)$_5$ | OH |
| 5/4 | CH$_3$ | H | (CH$_2$)$_7$ | OH |
| 5/5 | H | H | (CH$_2$)$_5$ | OH |

The starting ethyl or methyl ω-bromo esters are obtained commercially or were prepared from the commercially available ω-bromoacids as illustrated above for methyl 6-bromohexanoate.

Methyl 8-bromooctanoate is prepared from azelaic acid essentially as described in U.S. Pat. No. 3,852,419, or by direct esterification of 8-bromooctanoic acid as follows:

Methanol (4.7 L), 8-bromooctanoic acid (0.912 kg) and sulfuric acid (0.912 L) are charged into a suitable reactor and the mixture is heated in reflux temperature for 5 hours and is then stirred at ambient temperature overnight. The solvent is removed at reduced (3 mm Hg) pressure and the oily residue is dissolved in ether (4 L). The solution is washed with water (3×2 L), saturated NaHCO$_3$ solution (1 L) and brine (1 L). The ether portion is dried (MgSO$_4$) and filtered to remove dessicant. Evaporation of solvent followed by distillation of the crude oil gives methyl 8-bromooctanoate, b.p. 73°–76°/0.05 mm Hg, n$_D$$^{23}$ 1.4614.

EXAMPLE 6

Compounds of formula III wherein Im represents 1-imidazolyl, which are prepared according to the methods described herein.

| Compound | R″$_2$ | C$_q$H$_{2q}$ | X | R$_5$ |
|---|---|---|---|---|
| 6/1 | H | CH$_2$CH$_2$ | O | OEt |
| 6/2 | H | CH$_2$CH$_2$ | O | OH |
| 6/3 | H | CH$_2$CH$_2$ | S | OEt |
| 6/4 | H | CH$_2$CH$_2$ | S | OH |
| 6/5 | H | CH$_2$ | bond | OH |
| 6/6 | 5-Cl | CH$_2$CH$_2$ | O | OH |
| 6/7 | 5-OCH$_3$ | CH$_2$ | bond | OH |
| 6/8 | 5-CH$_3$ | CH$_2$CH$_2$ | O | OH |

The preparation of ethyl p-(2-bromoethoxy)-benzoate, the intermediate of formula V required for the synthesis of compounds 6/1, 6/2, 6/6 and 6/8 is described in U.S. Pat. No. 2,790,825. The corresponding thio starting material can be similarly prepared and used for compounds 6/3 and 6/4. The nitrile, 1-(4-cyanobenzyl)-3-methyl-2-(1-imidazolyl)-indole is prepared starting from the known p-cyanobenzyl bromide. Subsequent hydrolysis with a mixture of aqueous hydrochloric acid and glacial acetic acid yields the compound of example 6/5.

EXAMPLE 7

Treatment of 1-(5-methoxycarbonylpentyl)-2-(1-imidazolyl)-3-methylindole with lithium aluminum hydride in tetrahydrofuran at room temperature yields 1-(6-hydroxyhexyl)-2-(1-imidazolyl)-3-methylindole.

EXAMPLE 8

A solution of 4 g of 1-(4-methoxycarbonylbutyl)-3-methyl-2-(1-imidazolyl)indole in 40 ml of n-butanol is saturated with ammonia and heated on a steam bath in a pressure bottle for 3 days. The reaction mixture is evaporated to dryness and the product is crystallized to yield the 1-[4-carbamoylbutyl]-3-methyl-2-(1-imidazolyl)indole.

EXAMPLE 9

Preparation of 10,000 tablets each containing 10 mg of the active ingredient of Example 1:

| Formula | |
|---|---|
| 1-(4-carboxybutyl)-3-methyl-2-(1-imidazolyl)-indole hydrochloride | 100.00 g |
| Lactose | 1,157.00 g |
| Corn starch | 75.00 g |
| Polyethylene glycol 6,000 | 75.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave with 6.4 mm diameter, uppers bisected.

EXAMPLE 10

Preparation of 10,000 capsules each containing 25 mg of the active ingredient of Example 11:

| Formula | |
|---|---|
| 1-(5-carboxypentyl)-3-methyl-2-(1-imidazolyl)-indole hydrochloride | 250.0 g |
| Lactose | 1,650 g |

Procedure

All the powders are passed through a screen with openings of 0.6 mm. Then the drug substance is placed in a suitable mixer and mixed first with the talcum, then with the lactose until homogenous. No. 3 capsules are filled with 200 mg, using a capsule filling machine.

What is claimed is:

1. A compound of the formula

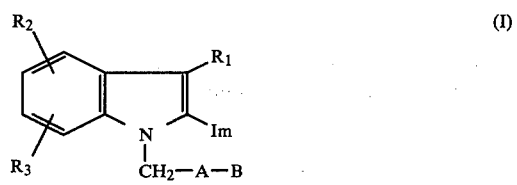

(I)

wherein
R$_1$ represents hydrogen or lower alkyl;
Im represents 1-imidazolyl unsubstituted or substituted by lower alkyl, carboxy, lower alkoxycarbonyl or carbamoyl;
R$_2$ and R$_3$ independently represent hydrogen, lower alkyl, halogen, trifluoromethyl, hydroxy, lower alkoxy, lower alkyl-(thio, sulfinyl or sulfonyl); or
R$_2$ and R$_3$ together when attached to adjacent carbons represent lower alkylenedioxy;
A represents straight chain or branched alkylene of 1 to 12 carbon atoms, alkenylene of 2 to 12 carbon atoms, alkynylene of 2 to 12 carbon atoms, lower alkylenephenylene lower alkylene, lower alkylenephenylene, phenylene lower alkylene, phenylene, a direct bond, lower alkylene-(thio or oxy)-lower alkylene, lower alkylene-(thio or oxy)-phenylene;

B represents carboxy, lower alkoxycarbonyl, carbamoyl, mono- or di- lower alkylcarbamoyl, cyano or hydroxymethyl; the N-oxide thereof; or a pharmaceutically acceptable salt thereof.

2. A compound of claim 1 wherein $R_1$ represents hydrogen or lower alkyl;

Im represents 1-imidazolyl unsubstituted or substituted by lower alkyl;

$R_2$ is hydrogen, lower alkyl, halogen, trifluoromethyl, hydroxy, lower alkoxy;

$R_3$ is hydrogen;

A represents straight chain or branched alkylene of 1 to 12 carbon atoms, phenylene, lower alkylenephenylene of 7 to 10 carbon atoms or lower alkylene-(thio or oxy)-phenylene of 7 to 10 carbon atoms, or a direct bond;

B represents carboxy, lower alkoxycarbonyl, carbamoyl, cyano or hydroxymethyl; the N-oxide thereof; or a pharmaceutically acceptable salt thereof.

3. A compound of claim 1 of the formula

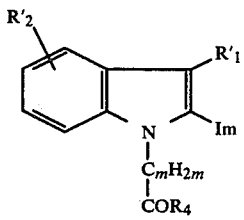

(II)

wherein $R_1'$ represents hydrogen or lower alkyl;

$R_2'$ represents hydrogen, lower alkyl, halogen, trifluoromethyl, hydroxy or lower alkoxy;

Im represents 1-imidazolyl;

m represents an integer from 1 to 13;

$R_4$ represents hydroxy, lower alkoxy or amino; or a pharmaceutically acceptable salt thereof.

4. A compound of claim 1 of the formula

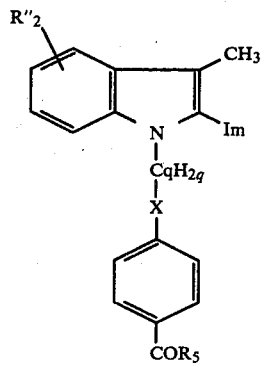

(III)

wherein $R_2''$ represents hydrogen, methyl, chloro, fluoro, trifluoromethyl, hydroxy or methoxy;

q represents an integer from 1 to 4;

X=oxygen, sulfur or a direct bond;

$R_5$ represents hydroxy or lower alkoxy;

Im represents 1-imidazolyl; or a pharmaceutically acceptable salt thereof.

5. A compound of claim 1 being 1-(4-carboxybutyl)-3-methyl-2-(1-imidazolyl)-indole or a pharmaceutically acceptable acid addition, metal or ammonium salt thereof.

6. A compound of claim 1 being 1-(5-carboxypentyl)-3-methyl-2-(1-imidazolyl) indole or a pharmaceutically acceptable acid addition, metal or ammonium salt thereof.

7. A pharmaceutical composition suitable for oral or parenteral administration to mammals for the treatment or prevention of diseases responsive to inhibition of thromboxane synthetase comprising an effective amount of a compound of claim 1 in combination with one or more pharmaceutically acceptable carriers.

8. A method of selectively inhibiting the synthesis of thromboxane in mammals comprising the administration to said mammal of an effective amount of a compound of claim 1 in combination with one or more pharmaceutically acceptable carriers.

9. A method of treating diseases responsive to thromboxane synthetase inhibition in mammals comprising the administration to a mammal in need thereof of a therapeutically effective amount of a compound of claim 1 in combination with one or more pharmaceutically acceptable carriers.

* * * * *